United States Patent
Dave et al.

(10) Patent No.: US 9,247,731 B2
(45) Date of Patent: Feb. 2, 2016

(54) ARYLOXYPHENOXYPROPIONIC ACID HERBICIDE EMULSIFIABLE CONCENTRATES WITH NON-PETROLEUM DERIVED BUILT-IN ADJUVANT

(75) Inventors: Hiteshkumar Dave, Carmel, IN (US); Lei Liu, Carmel, IN (US); Raymond E. Boucher, Jr., Lebanon, IN (US); David G. Ouse, Indianapolis, IN (US); Richard K. Mann, Franklin, IN (US); James M. Gifford, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/529,236

(22) Filed: Jun. 21, 2012

(65) Prior Publication Data

US 2012/0329651 A1    Dec. 27, 2012

Related U.S. Application Data

(60) Provisional application No. 61/499,879, filed on Jun. 22, 2011.

(51) Int. Cl.
*A01N 25/02* (2006.01)
*A01N 39/02* (2006.01)
*A01N 25/04* (2006.01)

(52) U.S. Cl.
CPC .............. *A01N 25/02* (2013.01); *A01N 25/04* (2013.01)

(58) Field of Classification Search
USPC ........................................................ 504/311
See application file for complete search history.

(56) References Cited

U.S. PATENT DOCUMENTS

| 2007/0184980 A1* | 8/2007 | Roberts et al. | ................ 504/118 |
| 2008/0254983 A1 | 10/2008 | Panayi et al. | |
| 2009/0062127 A1* | 3/2009 | Liu | ................ 504/361 |
| 2011/0098181 A1 | 4/2011 | Mann et al. | |

FOREIGN PATENT DOCUMENTS

| CN | 101401569 A | 4/2009 | |
| CN | 101606517 A | 12/2009 | |
| CN | 101785457 A | 7/2010 | |
| CN | 101785465 A | 7/2010 | |
| CN | 101953340 A | 1/2011 | |
| CN | 101961011 A | 2/2011 | |
| CN | 102027902 A2 | 4/2011 | |
| EP | 307502 A1 * | 3/1989 | ............... C07F 9/18 |
| WO | 2005048706 A2 | 6/2005 | |

OTHER PUBLICATIONS

Ntanos et al., "Barnyardgrass (Echinochloa crus-galli) Control in Water-Seeded Rice (Oryza sativa) with Cyhalofop-butyl", 2000, Weed Technology, vol. 14, issue 2, pp. 383-388.*
Prashant Jha et al., "Cyhalofop application timing and adjuvant selection for Echinochloa crus-galli control in rice", Crop Protection; vol. 29, No. 8, Aug. 1, 2010, pp. 820-823.
JJ Schott et al., "Effects of adjuvants on herbicidal action. III. Effects of petroleum and rapeseed oils on diclofop-methyl action on ryegrass", Agronomie, vol. 11, No. 1, Jan. 1, 1991, pp. 27-34.
European Search Report issued in EP application No. 12802881.8 on Dec. 16, 2014.

* cited by examiner

*Primary Examiner* — Michael B Pallay
(74) *Attorney, Agent, or Firm* — Michael R. Asam; Meunier Carlin & Curfman, LLC

(57) ABSTRACT

Herbicide emulsifiable concentrates containing an aryloxyphenoxypropionic acid herbicide and a non-petroleum derived built-in adjuvant such as a plant-derived methylated seed oil or a vegetable oil concentrate are useful for controlling undesirable vegetations, and exhibit improved herbicidal efficacy on weeds, particularly in an aquatic environment such as in flooded rice paddy or field.

20 Claims, No Drawings

US 9,247,731 B2

ARYLOXYPHENOXYPROPIONIC ACID HERBICIDE EMULSIFIABLE CONCENTRATES WITH NON-PETROLEUM DERIVED BUILT-IN ADJUVANT

CROSS REFERENCE TO RELATED APPLICATIONS

This application claims the benefit of U.S. Provisional Application No. 61/499,879, filed Jun. 22, 2011, the entirety of which is incorporated herein by reference.

FIELD

This present invention concerns herbicide emulsifiable concentrates containing a grass-active herbicide and non-petroleum derived built-in adjuvant. Such emulsifiable concentrates exhibit improved herbicidal efficacy on weeds in flooded paddy rice applications.

BACKGROUND

Agrochemical formulations are generally designed based on customer needs and the physiochemical properties of the active ingredients, for example, the solubility of the active ingredient in water or non-aqueous solvents. There are two major categories of formulations, solid formulations and liquid formulations.

Emulsifiable concentrates (EC) containing agricultural active ingredients, represent one class of liquid formulations that are routinely used to control weeds and pests in agriculture. Active ingredients, in the form of solids or liquids, may be formulated as emulsifiable concentrates and include insecticides, herbicides, fungicides and nematicides. EC formulations may contain, in addition to the dissolved active ingredient, a water immiscible solvent, one or more surfactants, an adjuvant and other inert ingredients. The EC may be diluted with a carrier solvent such as water at the point of use for spray application to control pests or weeds or may be applied directly to the area of interest, such as for example, to water flooded paddy rice.

Adjuvants are important components of EC formulations and are defined as substances which can increase the biological activity of the active ingredient, but are themselves not significantly biologically active. Adjuvants assist with the effectiveness of the active ingredient such as, for example, by improving the delivery and uptake of an herbicide into a target weed plant leading to improved biological control.

Adjuvants, in the form of solids or liquids, can be added directly to a formulated agricultural product, such as an EC, to provide improved performance of the product upon application. Commonly used adjuvants may include, for example, surfactants, spreaders, petroleum and plant derived oils and solvents, and wetting agents. Examples of commonly used adjuvants include, but are not limited to, paraffin oil, horticultural spray oils (e.g., summer oil), methylated rape seed oil, methylated soybean oil, highly refined vegetable oil and the like, polyol fatty acid esters, polyethoxylated esters, ethoxylated alcohols, alkyl polysaccharides and blends, amine ethoxylates, sorbitan fatty acid ester ethoxylates, polyethylene glycol esters, organosilicone based surfactants, ethylene vinyl acetate terpolymers, ethoxylated alkyl aryl phosphate esters and the like. These and other adjuvants are described in the "*Compendium of Herbicide Adjuvants, 9th Edition*," edited by Bryan Young, Dept. of Plant, Soil and Agricultural Systems, Southern Illinois University MC-4415, 1205 Lincoln Drive, Carbondale, IL 62901.

The term "built-in adjuvant" refers to one or more adjuvants that have been added to a particular formulation, such as a liquid or granule formulation, at the manufacturing stage of the product, rather than at the point of use of the product such as, for example, to a spray solution. The use of built-in adjuvants simplifies the use of agrochemical products for the end-user by reducing the number of ingredients that must be individually measured and applied.

Rice is an important cereal crop grown in many parts of the world and is cultivated under both wet and dry conditions. Control of noxious weeds in rice is very important in order to maintain high levels of agricultural productivity. Use of herbicide emulsifiable concentrates for weed control in flooded paddy rice is a very common agronomic practice in many rice growing regions. New herbicide products that offer improved performance relative to current products are in constant demand.

Cyhalofop-butyl, (2R)-2-[4-(4-cyano-2-fluorophenoxy)phenoxy]propanoic acid (CAS#122008-78-0), is a member of the aryloxyphenoxypropionic acid class of herbicides which are known in the art as the fop herbicides and is used to control grass weeds in rice. Cyhalofop-butyl is marketed as Clincher® herbicide (registered trademark of Dow AgroSciences LLC) and is sold in granule (GR), oil in water (EW) and emulsifiable concentrate (EC) formulations and exhibits good selectivity to rice when used in both dry land and flooded paddy applications.

Existing commercial EC formulations containing cyhalofop-butyl also contain relatively large amounts of petroleum derived solvents that serve primarily to dissolve the active ingredient. The solvent may contribute greater than 50 percent by weight (wt %) of the total formulation in currently marketed EC products containing cyhalofop-butyl. The use of petroleum derived solvents in these products can limit the biological performance of cyhalofop-butyl herbicide due to a minimal herbicidal adjuvant effect. Petroleum derived solvents may also present safety and handling issues due to their flammability and toxicity.

The present invention provides an improvement to EC herbicide products containing grass-active herbicides by the use of the relatively safer non-petroleum derived built-in adjuvants. Such EC compositions offer improved herbicidal efficacy on weeds in flooded paddy rice applications and improved safety to the applicator and the environment.

SUMMARY

The present invention concerns an emulsifiable herbicide concentrate containing built-in adjuvant which comprises:
a) an aryloxyphenoxypropionic acid herbicide comprising, with respect to the total composition, from about 25 gram per liter (g/L) to about 225 g/L;
b) a non-petroleum derived built-in adjuvant comprising, with respect to the total composition, from about 600 g/L to about 950 g/L; and
c) a surfactant comprising, with respect to the total composition, from about 10 g/L to about 150 g/L.
wherein the weight ratio of the herbicide to the non-petroleum derived built-in adjuvant is from about 1:3 to about 1:33.

Another aspect of the present invention concerns a method of controlling undesirable vegetation in an aquatic environment which comprises spraying, pouring or adding the emulsifiable herbicide concentrate, or a dilution thereof, into the aquatic environment either before emergence or after emergence of the undesirable vegetation.

DETAILED DESCRIPTION

Agricultural active ingredients that have low water solubility can sometimes be difficult to effectively apply to crops to eliminate pests. This situation is particularly challenging when the active ingredients are not applied directly to plant foliage such as, for example, when EC products containing herbicides are used to control weeds in flooded paddy rice. Herbicide EC products that are applied to flooded paddy rice are normally added directly to the water in the paddy rice and have very little direct contact with plant foliage during application. Cyhalofop-butyl is an herbicidal active ingredient that when applied to water as an EC, requires the use of an organic solvent that may serve as both a carrier and a built-in adjuvant to provide the necessary delivery and uptake of the herbicide into the target weeds and expression of acceptable levels of weed control. Emulsifiable concentrates containing cyhalofop-butyl that are currently marketed for the control of weeds in flooded paddy rice contain petroleum derived built-in adjuvants such as, for example, aromatic solvents or oils like ditridecyl phthalate.

It has now been found that emulsifiable concentrates containing an aryloxyphenoxypropionic acid herbicide, a non-petroleum derived built-in adjuvant such as, for example, a plant-derived methylated seed oil or a vegetable oil concentrate, and a surfactant, surprisingly offer improved weed control in aquatic environments such as, for example, flooded paddy rice on a grams active ingredient per hectare (gai/ha) basis. The improved weed control has been found to depend on the weight ratio of the herbicide active ingredient to the non-petroleum derived built-in adjuvant.

The emulsifiable herbicide concentrate of the present invention is comprised of an aryloxyphenoxypropionic acid herbicide active ingredient, a non-petroleum derived built-in adjuvant and a surfactant.

The aryloxyphenoxypropionic acid herbicide active ingredient of the present invention may include, but is not limited to, cyhalofop-butyl, fenoxaprop-ethyl, fluazifop-P-butyl, haloxyfop-methyl, haloxyfop-R-methyl, metamifop, propaquizafop, quizalofop-P-ethyl, and quizalofop-P-tefuryl. Preferred aryloxyphenoxypropionic acid herbicide active ingredients of the present invention include cyhalofop-butyl, fenoxaprop-ethyl, haloxyfop-methyl, haloxyfop-R-methyl and metamifop. The aryloxyphenoxypropionic acid herbicide active ingredient of the present invention comprises, with respect to the total composition, from about 25 gai/L to about 225 gai/L, preferably from about 25 gai/L to about 150 gai/L.

The non-petroleum derived built-in adjuvant of the present invention may be in the form of a water immiscible liquid and may serve as both the solvent and the built-in adjuvant in the emulsifiable herbicide concentrate. Water immiscible liquids that may be used in the present invention generally have less than about 1 volume percent solubility in water and may include, but are not limited to, one or more plant, algae or animal derived oils such as, but not limited to, seed oils, vegetable oils, animal oils and esters thereof.

Preferred non-petroleum derived built-in adjuvants of the present invention include soybean oil, rape seed oil, olive oil, castor oil, sunflower seed oil, coconut oil, corn oil, cotton seed oil, linseed oil, palm oil, peanut oil, safflower oil, sesame oil, tung oil and the like, and $C_1$-$C_{10}$ esters of the above plant derived oils such as methyl soyate, 2-ethyl hexyl stearate, n-butyl oleate, isopropyl myristate, propylene glycol dioleate and the like. The non-petroleum derived built-in adjuvant of the present invention comprises, with respect to the total composition, from about 600 g/L to about 950 g/L, preferably from about 600 g/L to about 850 g/L.

The weight ratio of the herbicide active ingredient to the non-petroleum derived built-in adjuvant of the present invention has unexpectedly been found to affect the herbicidal efficacy of the composition when used to control weeds in paddy rice. The weight ratio of the herbicide active ingredient to the non-petroleum derived built-in adjuvant offers improved herbicidal efficacy in the range from about 1:3 to about 1:33, most preferably from about 1:4 to about 1:33.

The surfactant of the present invention may be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(octyl) sulfo-succinate; sorbitol esters, such as sorbitol oleate; quaternary amines, such as lauryl trim-ethyl-ammonium chloride; polyethylene glycol esters of fatty acids, such as polyethylene glycol stearate; block copolymers of ethylene oxide and propylene oxide; salts of mono and dialkyl phosphate esters; and mixtures thereof. The surfactant of the present invention comprises, with respect to the total composition, from about 10 g/L to about 150 g/L, preferably from about 50 g/L to about 150 g/L.

In a typical procedure for preparing the emulsifiable herbicide concentrate of the present invention a water immiscible solution is prepared by mixing together the oil soluble ingredients including, but not limited to, one or more of the non-petroleum derived built-in adjuvant, an emulsifying surfactant and the oil soluble aryloxyphenoxypropionic acid herbicide active ingredient to provide a emulsifiable concentrate containing the ingredients at the desired concentrations.

An example of an emulsifiable herbicide concentrate of the present invention comprises:

a) an aryloxyphenoxypropionic acid herbicide active ingredient comprising, with respect to the total composition, from about 25 g/L to about 225 g/L of cyhalofop-butyl;

b) a non-petroleum derived built-in adjuvant comprising, with respect to the total composition, from about 600 g/L to about 950 g/L of methyl soyate; and c) a surfactant comprising, with respect to the total composition, from about 10 g/L to about 150 g/L of Polyglycol 26-2;

wherein the weight ratio of cyhalofop-butyl to methyl soyate is from about 1:3 to about 1:33.

Another aspect of the present invention concerns a method of controlling undesirable vegetation by applying the emulsifiable herbicide concentrate of the present invention to an aquatic environment such as rice paddys or fields, ponds, lakes and streams and the like, for the control of undesirable vegetation. The application may be by any normal means such as, for example, by pouring, spraying or adding the concentrate to the aquatic environment. In this aspect a herbicidally effective amount of the emulsifiable herbicide concentrate is applied, with or without prior dilution, to an area of water to provide suitable control of undesirable vegetation. The emulsifiable herbicide concentrate of the present invention is particularly useful for the control of grass weeds in flooded rice paddys or fields and offers improved herbicidal performance relative to current emulsifiable concentrate products that contain petroleum derived adjuvants and are used to control grass weeds in flooded rice paddys or fields.

In addition to the compositions set forth above, the present invention also embraces compositions containing one or more additional pesticide active ingredients, plant growth regulators or safeners that are added to the emulsifiable herbicide concentrate of the present invention. These pesticide active ingredients, plant growth regulators and safeners may include one or more of an herbicide, an insecticide, a fungicide, a plant growth regulator and an herbicide safener. These additional pesticide active ingredients may be soluble, partially soluble or insoluble in the emulsifiable concentrate of the present invention.

Suitable herbicides that may be added to the emulsifiable herbicide concentrate of the present invention may be selected from clodinafop-propargyl, clethodim, cycloxydim, diclofop-methyl, fenoxaprop-ethyl+isoxidifen-ethyl, pinoxaden, profoxydim, sethoxydim, tepraloxydim, tralkoxydim, 2,4-D esters and salts, 2,4-MCPA, 2,4-MCPA esters and salts, acetochlor, acifluorfen, alachlor, amidosulfuron, aminopyralid, aminotriazole, ammonium thiocyanate, anilifos, azimsulfuron, benfuresate, bensulfuron-methyl, bentazon, bentazone-sodium, benthiocarb, benzobicyclon, benzofenap, bifenox, bispyribac-sodium, bromobutide, butachlor, cafenstrole, carfentrazone-ethyl, chlorimuron, chlorpropham, cinosulfuron, clomazone, clomeprop. clopyralid, cloransulam-methyl, cyclosulfamuron, cumyluron, daimuron, diclosulam, diflufenican, dimepiperate, dimethametryn, diquat, dithiopyr, EK2612, EPTC, esprocarb, ET-751, ethoxysulfuron, ethbenzanid, fenoxasulfone, fentrazamide, flazasulfuron, florasulam, fluazifop, flucetosulfuron, flufenacet, flufenpyr-ethyl, flumetsulam, flumioxazin, flupyrsulfuron, fluoroxypyr, fluoroxypyr esters and salts, fomesafen, foramsulfuron, glufosinate, glufosinate-P, glyphosate, halosulfuron-methyl, imazamethabenz, imazamox, imazapic, imazapyr, imazaquin, imazethapyr, imazosulfuron, indanofan, ioxynil, ipfencarbazone, MCPB, mefenacet, mesosulfuron, mesotrione, metazosulfuron, metolachlor, metosulam, metsulfuron, molinate, monosulfuron, MSMA, orthosulfamuron, oryzalin, oxadiargyl, oxadiazon, oxazichlomefone, oxyfluorfen, pendimethalin, penoxsulam, pentoxazone, pethoxamid, picloram, piperophos, pretilachlor, primisulfuron, prohexadione-calcium, propachlor, propanil, propisochlor, propyrisulfuron, prosulfuron, pyrabuticarb, pyraclonil, pyrazogyl, pyrazolynate, pyrazosulfuron-ethyl, pyrazoxyfen, pyribenzoxim, pyridate, pyriftalid, pyriminobac-methyl, pyrimisulfan, pyroxsulam, quinoclamine, quinclorac, S-3252, simazine, simetryne, s-metolachlor, sulcotrione, sulfentrazone, sulfosate, tefuryltrione, thenylchlor, thiazopyr, thiobencarb, triafamone, triclopyr esters and salts, trifluralin, trinexapac-ethyl, tritosulfuron and compounds of the following generic structures and their derivatives as disclosed in U.S. Pat. Nos. 7,314,849 B2 and 7,300,907 B2

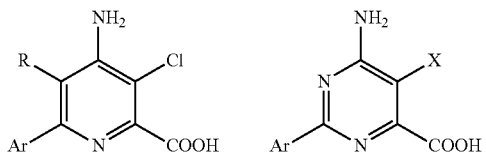

wherein Ar is a polysubstituted phenyl group and R is H or halo and X is halo. Especially suitable herbicides that may be added to the emulsifiable herbicide concentrate of the present invention include penoxsulam and bensulfuron-methyl.

Suitable insecticides that may be added to the emulsifiable herbicide concentrate of the present invention may be selected from abamectin, acephate, acetamiprid, acrinathrin, alpha-cypermethrin, alpha-endosulfan, azadirachtin, azinphos-ethyl, azinphos-methyl, bendiocarb, benfuracarb, bensultap, beta-cyfluthrin, beta-cypermethrin, bifenthrin, bufencarb, buprofezin, butacarb, cadusafos, carbaryl, carbofuran, carbosulfan, cartap, cartap hydrochloride, chlorantraniliprole, chlorfenapyr, chlorfenvinphos, chlorfluazuron, chlormephos, chlorpyrifos, chlorpyrifos-methyl, chromafenozide, clothianidin, cyantraniliprole, cyfluthrin, cyhalothrin, cypermethrin, deltamethrin, diazinon, dicrotophos, diflubenzuron, dimethoate dinotefuran, disulfoton, emamectin, emamectin benzoate, endosulfan, endothion, endrin, EPN, esfenvalerate, etaphos, ethiofencarb, ethion, ethiprole, ethoate-methyl, etofenprox, fenamiphos, fenazaflor, fenethacarb, fenitrothion, fenobucarb, fenpropathrin, fensulfothion, fenthion, fenthion-ethyl, fenvalerate, fipronil, flonicamid, flubendiamide, flucythrinate, fonofos, fufenozide, furathiocarb, gamma-cyhalothrin, gamma-HCH, halfenprox, halofenozide, heptenophos, hyquincarb, imidacloprid, indoxacarb, isazofos, isobenzan, isocarbophos, isofenphos, isofenphos-methyl, isoprocarb, isothioate, isoxathion, kinoprene, lambda-cyhalothrin, lepimectin, lufenuron, malathion, methamidophos, methomyl, methoxyfenozide, mevinphos, mexacarbate, milbemectin, monocrotophos, nitenpyram, novaluron, omethoate, oxamyl, oxydemeton-methyl, oxydeprofos, oxydisulfoton, parathion, parathion-methyl, penfluoron, permethrin, phenthoate, phorate, phosalone, phosfolan, phosmet, phosphamidon, pirimetaphos, pirimicarb, pirimiphos-ethyl, pirimiphos-methyl, primidophos, profenofos, profluthrin, promecarb, propaphos, propoxur, prothiofos, pymetrozine, pyrafluprole, pyridalyl, pyrifluquinazon, pyriprole, pyriproxyfen, spinetoram, spinosad, spirotetramat, sulfoxaflor, sulprofos, tau-fluvalinate, tebufenozide, tebufenpyrad, teflubenzuron, tefluthrin, tetramethylfluthrin, theta-cypermethrin, thiacloprid, thiamethoxam, thicrofos, thiocyclam, thiocyclam oxalate, thiodicarb, thiometon, thiosultap, thiosultap-disodium, thiosultap-monosodium, thuringiensin, tolfenpyrad, triazophos, trifluumuron and zeta-cypermethrin.

Suitable fungicides that may be added to the emulsifiable herbicide concentrate of the present invention may be selected from tricyclazole, phthalide, carpropamide, pyroquilon, diclocymet, fenoxanil, probenazole, isoprothiolane, iprobenfos, isotianil, tiadinil, kasugamycin, flutolanil, mepronil, pencycuron, polyoxins, validamycin, toclophosmethyl, boscalid, penthiopyrad, thifluzamide, bixafen, fluopyram, isopyrazam, propiconazole, difenoconazole, fenbuconazole, ipconazole, triadimefon, hexaconazole, azoxystrobin, metaminostrobin, orysastrobin, trifloxystrobin and acibenzolar-S-methyl. Some of these fungicides may not be effective for disease control when applied at the timing of the herbicide application because fungal disease propagation and growth cycles may not match the targeted weed growth cycles. The effective use and application timing of these fungicides can be easily determined by one of normal skill in the art.

Suitable herbicide safeners that may be added to the emulsifiable herbicide concentrate of the present invention may be selected from benoxacor, benthiocarb, cloquintocet-mexyl, daimuron, dichlormid, dicyclonon, dimepiperate, fenchlorazole-ethyl, fenclorim, flurazole, fluxofenim, furilazole, Harpin proteins, isoxadifen-ethyl, mefenpyr-diethyl, mephenate, MG 191, MON 4660, naphthalic anhydride (NA), oxabetrinil, R29148 and N-phenyl-sulfonylbenzoic acid amides.

Suitable plant growth regulators that may be added to the emulsifiable herbicide concentrate of the present invention may be selected from 2,4-D, 2,4-DB, IAA, IBA, naphthaleneacetamide, α-naphthaleneacetic acid, kinetin, zeatin, ethephon, aviglycine, 1-methylcyclopropene (1-MCP), ethephon, gibberellins, gibberellic acid, abscisic acid, ancymidol, flurprimidol, mefluidide, paclobutrazol, tetcyclacis, uniconazole, brassinolide, brassinolide-ethyl and ethylene.

In addition to the compositions and uses set forth above, the present invention also embraces the composition and use of the emulsifiable herbicide concentrate in combination with one or more additional compatible ingredients. These additional compatible ingredients may include, for example, one or more agrochemical active ingredients, surfactants, dyes, fertilizers and micronutrients, growth regulators and pheromones and any other additional ingredients providing functional utility, such as, for example, stabilizers, fragrant, defoamers and dispersants.

In addition to pouring, dribbling, bottle shaking and direct injection application, the emulsifiable herbicide concentrate of the present invention may optionally be diluted in a spray tank containing water carrier and the resulting aqueous mixture used for spray application to control weeds.

When the compositions of the present invention are used in combination with additional active ingredients the presently claimed compositions can be formulated with the additional active ingredient or active ingredients as premix concentrates, they may be tank mixed with the additional active ingredient or active ingredients for spray or pour application or they may be applied sequentially with the additional active ingredient or active ingredients in separate spray or pour applications.

The following examples are presented to illustrate the various aspects of this invention and should not be construed as limitations to the claims.

EXAMPLE 1

Preparation of Emulsifiable Concentrates of the Present Invention

The emulsifiable concentrates of the present invention are prepared by mixing molten cyhalofop-butyl with methyl soyate adjuvant (Agnique® ME 18S-U; registered trademark of Cognis) and an emulsifier to provide the compositions shown in Table 1.

TABLE 1

Emulsifiable Concentrates of the Present Invention

| | Sample | | |
|---|---|---|---|
| Ingredients | A[1] (wt %) | B (wt %) | C (wt %) |
| cyhalofop-butyl | 13.44 | 13.44 | 8.06 |
| methyl soyate | 0 | 76.16 | 81.54 |
| emulsifier (Emgard ® 2033-C)[2] | 0 | 10.40 | 10.40 |
| emulsifier (Toximul ® DH68/Toximul ® DL66)[3] | 3.12/7.28 | 0 | 0 |
| Aromatic 100 | 76.16 | 0 | 0 |

[1]Sample A was prepared for comparison to inventive compositions Sample B and Sample C;
[2]Emgard is a registered trademark of Cognis;
[3]Toximul is a registered trademark of Stepan Company.

EXAMPLE 2

Use of the Emulsifiable Concentrate of the Present Invention for Weed Control in Simulated Rice Paddys Simulated Rice Paddy Preparation: Two kg of mineral soil and 500 ml of distilled water were added to the container (4.163 L (1.1 gallon), 15 cm ht×20.55 cm diameter, HDPE round container; for treatment purposes the surface area is calculated as 331 cm$^2$ with 1 hectare equivalent to 10$^8$ cm$^2$) and thoroughly mixed with a spatula for about 5 minutes to create a smooth mud mix. Once the mud is mixed, a 3 cm. furrow is made across the middle of the container to which is added 18 g (0.6 oz.) Osmocote® (registered trademark of The Scotts Company LLC or its affiliates; 17:6:10 N:P:K). The furrow is then sealed keeping the Osmocote® below the surface of the soil.

Plant Propagation

Weed Plant—Chinese sprangletop, *Leptochloa chinensis* (LEFCH): In a small container, 80 grams of mineral soil is mixed with 40 milliliters (mL) of distilled water to make a viscous slurry. ¼ tsp (2-4000) of Leptochloa seed is added to the slurry and thoroughly mixed to evenly distribute the seed. Approximately 3 grams of this slurry is placed atop the prepared mud on one side of each container and spread thinly in a 1-2 cm band across the container. This yields 25-50 plants per pot. Clear shrink wrap is used to cover the containers acting as a terrarium. The wrap is held in place by masking tape until the Leptochloa seed germinates, about 5 days. The covered pots are kept in the greenhouse at a constant temperature of 18 to 22° C. and 50 to 60% relative humidity. Natural light was supplemented with 1000-watt metal halide overhead lamps with an average illumination of 500 microeinsteins (μE) m$^{-2}$ s$^{-1}$ photosynthetic active radiation (PAR). Day length was 16 hours.

Weed Plant—Barnyard grass, *Echinochloa crus-galli* (ECHCG): Once the sprangletop seed has germinated, a shallow depression is made in the mud parallel to the sprangletop. Barnyard grass seed is sprinkled along this trench and then covered with white sand. This yields approximately 20-30 plants per pot. At this stage, the plant material is top-watered with distilled water and kept very moist. Pots are moved to a warmer greenhouse where the temperature is kept at 26 to 28° C. with the same lighting parameters as described for the Chinese sprangletop.

Crop Plant—Paddy rice, *Oryza sativa* subsp. *japonica* var. M202 (ORYSJ): On the same day that the barnyard grass is planted, the rice is also directly seeded into the pot mud following the same methodology. A shallow depression is made in the mud parallel to the Chinese sprangletop and Barnyard grass and the seed is sprinkled along this trench then covered with white sand. This should also yield approximately 5 to 8 plants per pot.

The plants are allowed to grow until they reach 6-8 cm height in about 8 days.

Flooding and Paddy Application Methods for Herbicide Evaluations

Once the plants have reached the proper size (the growth stage of the various species ranged from 2 to 4 leaves) the containers are flooded with distilled water to a depth of 3 cm leaving 1-2 cm of each plant above the surface. Herbicide treatments are applied directly to the paddy water as liquid formulations at rates adjusted to the surface area. Treatments were replicated 2-3 times. At intervals, percent visual injury and weed control assessments were made on a scale of 0 to 100% compared to the untreated control plants (where 0 is equal to no injury or control and 100 is equal to complete death of the plant).

TABLE 2

Crop Tolerance and Percent Weed Control with Cyhalofop-butyl Emulsifiable Concentrates of the Present Invention 21 days After Application in a Simulated Rice Paddy Trial in the Greenhouse

| Herbicide Active Ingredient (ai) | Treatment Description | Application Rate (g ai/ha) | Average % Injury to Plants[1] | | |
|---|---|---|---|---|---|
| | | | ORYSJ | LEFCH | ECHCG |
| cyhalofop-butyl | Sample A | 45 | 2 | 0 | 0 |
| | | 90 | 5 | 0 | 0 |
| | | 180 | 1 | 30 | 20 |
| | | 360 | 2 | 70 | 80 |
| cyhalofop-butyl | Sample B | 45 | 1 | 5 | 0 |
| | | 90 | 3 | 38 | 15 |
| | | 180 | 4 | 20 | 35 |
| | | 360 | 4 | 75 | 70 |
| cyhalofop-butyl | Sample C | 45 | 2 | 0 | 0 |
| | | 90 | 2 | 5 | 5 |
| | | 180 | 4 | 55 | 65 |
| | | 360 | 8 | 80 | 100 |
| cyhalofop-butyl | Clincher ® CA[2] | 45 | 0 | 0 | 0 |
| | | 90 | 1 | 0 | 0 |
| | | 180 | 3 | 10 | 25 |
| | | 360 | 5 | 60 | 63 |

[1]ORYSJ = Paddy rice, *Oryza sativa* subsp. *japonica* var. M202 LEFCH = Chinese sprangletop, *Leptochloa chinensis* ECHCG = Barnyard grass, *Echinochloa crus-galli*
[2]Clincher ® CA (registered trademark of Dow AgroSciences LLC) is an EC formulation containing 285 grams per liter of cyhalofop-butyl

What is claimed:

1. A herbicidal composition comprising:
   a) from about 25 gram per liter (g/L) to about 225 g/L, with respect to the composition, of an aryloxyphenoxypropionic acid herbicide;
   b) from about 600 g/L to about 950 g/L, with respect to the composition, of a non-petroleum derived built-in adjuvant; and
   c) from about 10 g/L to about 150 g/L, with respect to the composition, of a surfactant;
   wherein the weight ratio of the herbicide to the non-petroleum derived built-in adjuvant is from about 1:3 to about 1:33, and wherein the composition is an emulsifiable concentrate.

2. The composition of claim 1, wherein the aryloxyphenoxypropionic acid herbicide is cyhalofop-butyl, fenoxaprop-ethyl, fluazifop-P-butyl, haloxyfop-methyl, haloxyfop-R-methyl, metamifop, propaquizafop, quizalofop-P-ethyl, or quizalofop-P-tefuryl.

3. The composition of claim 1, wherein the aryloxyphenoxypropionic acid herbicide is cyhalofop-butyl.

4. The composition of claim 1, wherein the composition comprises from about 25 g/L to about 150 g/L, with respect to the composition, of the aryloxyphenoxypropionic acid herbicide.

5. The composition of claim 1, further comprising one or more additional inert ingredients.

6. The composition of claim 1, wherein the non-petroleum derived built-in adjuvant is at least one of a plant, algae or animal derived oil or a C1-C10 ester of a plant, algae or animal derived oil.

7. The composition of claim 6, wherein the C1-C10 ester of a plant, algae or animal derived oil is methyl soyate.

8. The composition of claim 1, wherein the composition comprises from about 600 g/L to about 850 g/L of the non-petroleum derived built-in adjuvant.

9. The composition of claim 1, wherein the surfactant is an alkyl sulfate salt, alkylarylsulfonate salt, alkylphenol-alkylene oxide addition product, soap, alkylnaphthalene-sulfonate salt, salt of a dialkyl ester of a sulfosuccinate, sorbitol ester, quaternary amine, polyethylene glycol ester of a fatty acid, block copolymer of ethylene oxide and propylene oxide, salt of a mono or dialkyl phosphate ester, or a mixture thereof 10. The composition of claim 1, wherein the composition comprises from about 50 g/L to about 150 g/L of the surfactant.

11. The composition of claim 1, wherein the weight ratio of the herbicide to the non-petroleum derived built-in adjuvant is from about 1:4 to about 1:33.

12. The composition of claim 1, wherein:
   (A) the aryloxyphenoxypropionic acid herbicide is cyhalofop-butyl, fenoxaprop-ethyl, fluazifop-P-butyl, haloxyfop-methyl, haloxyfop-R-methyl, metamifop, propaquizafop, quizalofop-P-ethyl, or quizalofop-P-tefuryl;
   (B) the non-petroleum derived built-in adjuvant is at least one of a plant, algae or animal derived oil or a $C_1$-$C_{10}$ ester of a plant, algae or animal derived oil; and
   (C) the surfactant is an alkyl sulfate salt, alkylarylsulfonate salt, alkylphenol-alkylene oxide addition product, soap, alkylnaphthalene-sulfonate salt, salt of a dialkyl ester of a sulfosuccinate, sorbitol ester, quaternary amine, polyethylene glycol ester of a fatty acid, block copolymer of ethylene oxide and propylene oxide, salt of a mono or dialkyl phosphate ester, or a mixture thereof.

13. The composition of claim 1, wherein the aryloxyphenoxypropionic acid herbicide is cyhalofop-butyl; the non-petroleum derived built-in adjuvant is methyl soyate; and the surfactant is polyglycol 26-2.

14. The composition of claim 1, further comprising one or more additional pesticide active ingredients.

15. The composition of claim 1, further comprising a herbicide safener.

16. A method of controlling undesirable vegetation comprising contacting the undesirable vegetation or the area adjacent thereof with the composition of claim 1 or a dilution thereof.

17. A method of controlling undesirable vegetation in an aquatic environment comprising
   (A) spraying foliage with the composition of claim 1 or dilution thereof or
   (B) pouring or adding the composition of claim 1 to the aquatic environment.

18. The method of claim 17, wherein the aquatic environment is a flooded rice paddy or field.

19. The method of claim 17, wherein (A) or (B) is performed before emergence of the undesirable vegetation.

20. The method of claim 17, wherein (A) or (B) is performed after the emergence of the undesirable vegetation.

* * * * *